(12) United States Patent
Baek et al.

(10) Patent No.: US 11,471,109 B2
(45) Date of Patent: Oct. 18, 2022

(54) METHODS AND DEVICES FOR RECOVERING DATA FROM AN AMPLITUDE-MODULATED SIGNAL

(71) Applicant: PHILIPS HEALTHCARE INFORMATICS, INC., Cambridge, MA (US)

(72) Inventors: David Boettcher Baek, San Diego, CA (US); Donald Bernard Lemersal, San Diego, CA (US); Lars Lading, Roskilde (DK)

(73) Assignee: CAPSULETECH, INC., San Diego, CA (US)

( * ) Notice: Subject to any disclaimer, the term of this patent is extended or adjusted under 35 U.S.C. 154(b) by 0 days.

(21) Appl. No.: 14/795,703

(22) Filed: Jul. 9, 2015

(65) Prior Publication Data

US 2017/0007186 A1    Jan. 12, 2017

(51) Int. Cl.
*A61B 5/00*     (2006.01)
*A61B 5/0535*   (2021.01)
(Continued)

(52) U.S. Cl.
CPC .............. *A61B 5/725* (2013.01); *A61B 5/021* (2013.01); *A61B 5/053* (2013.01); *A61B 5/0535* (2013.01);
(Continued)

(58) Field of Classification Search
None
See application file for complete search history.

(56) References Cited

U.S. PATENT DOCUMENTS 4,880,014 A * 11/1989 Zarowitz ............... A61B 5/00
                                                    600/547
7,385,443 B1 * 6/2008 Denison ................. H03F 3/38
                                                    330/10
(Continued)

FOREIGN PATENT DOCUMENTS

EP          1125359         8/2001
WO        2005122889       12/2005
(Continued)

OTHER PUBLICATIONS

Toro, Ross, Diagram of the Human Integumentary System (Infographic), Livescience.com, https://www.livescience.com/27990-human-body-systems-the-integumentary-system-infographic.html, Mar. 18, 2013 (Year: 2013).*

(Continued)

*Primary Examiner* — Matthew Kremer

(57) ABSTRACT

A device may be configured for performing signal processing in impedance sensing applications, and more specifically, for recovering data from an amplitude-modulated signal. In one aspect, a device includes a sensing circuit operable to sense an amplitude-modulated signal having a carrier frequency. The device also includes a mixer operable to mix the amplitude-modulated signal with a mixing signal having a mixing frequency to provide a frequency-downshifted signal having an intermediate frequency less than the carrier frequency. The device also includes a filter operable to filter the frequency-downshifted signal to provide a filtered signal. The device further includes a sampler operable to undersample the filtered signal at an undersampling frequency to provide a digital signal, the digital signal being representative of a modulating signal.

19 Claims, 8 Drawing Sheets

(51) Int. Cl.
*A61B 5/021* (2006.01)
*A61B 5/053* (2021.01)
*A61B 5/0295* (2006.01)

(52) U.S. Cl.
CPC .......... *A61B 5/6801* (2013.01); *A61B 5/7225* (2013.01); *A61B 5/0295* (2013.01); *A61B 5/6825* (2013.01); *A61B 2560/0214* (2013.01); *A61B 2562/04* (2013.01)

(56) References Cited

U.S. PATENT DOCUMENTS

| | | | |
|---|---|---|---|
| 7,941,213 B2 | 5/2011 | Markowitz et al. | |
| 8,059,758 B2* | 11/2011 | Filipovic | H03M 3/472 |
| | | | 375/324 |
| 8,364,250 B2 | 1/2013 | Moon et al. | |
| 8,412,317 B2 | 4/2013 | Mazar | |
| 8,449,471 B2 | 5/2013 | Tran | |
| 9,407,379 B2* | 8/2016 | Lau | H03D 7/1458 |
| 9,438,169 B2* | 9/2016 | Collier | H04B 1/26 |
| 9,488,730 B2* | 11/2016 | McConnell | G01S 19/21 |
| 2001/0044588 A1* | 11/2001 | Mault | A61B 5/14532 |
| | | | 600/549 |
| 2002/0011151 A1 | 8/2002 | Irion | |
| 2003/0004432 A1* | 1/2003 | Assenheimer | A61B 5/0536 |
| | | | 600/547 |
| 2005/0018201 A1* | 1/2005 | de Boer | G01B 9/02079 |
| | | | 356/479 |
| 2005/0197555 A1* | 9/2005 | Mouradian | A61B 5/0537 |
| | | | 600/365 |
| 2006/0085048 A1* | 4/2006 | Cory | A61B 5/0536 |
| | | | 607/48 |
| 2007/0208232 A1* | 9/2007 | Kovacs | A61B 5/6831 |
| | | | 600/300 |
| 2008/0129621 A1* | 6/2008 | Koshiji | A61B 5/411 |
| | | | 343/718 |
| 2008/0224688 A1* | 9/2008 | Rubinsky | A61B 5/05 |
| | | | 324/76.77 |
| 2009/0076346 A1* | 3/2009 | James | A61B 5/0006 |
| | | | 600/301 |
| 2009/0082691 A1 | 3/2009 | Denison | |
| 2009/0281414 A1 | 11/2009 | Feldman et al. | |
| 2010/0246420 A1* | 9/2010 | Tu | H04B 17/327 |
| | | | 370/252 |
| 2010/0246651 A1* | 9/2010 | Baheti | H03M 7/30 |
| | | | 375/224 |
| 2011/0074442 A1 | 3/2011 | Min et al. | |
| 2012/0157866 A1* | 6/2012 | Ross | A61B 5/0402 |
| | | | 600/509 |
| 2012/0165622 A1 | 6/2012 | Rodriguez et al. | |
| 2013/0023946 A1* | 1/2013 | Valvano | A61B 5/0538 |
| | | | 607/18 |
| 2013/0044826 A1 | 2/2013 | Walker | |
| 2013/0190599 A1* | 7/2013 | Wyeth | A61B 5/05 |
| | | | 600/409 |
| 2013/0331678 A1* | 12/2013 | Lading | A61B 5/7278 |
| | | | 600/393 |
| 2013/0338473 A1* | 12/2013 | Bohorquez | A61B 5/053 |
| | | | 600/393 |
| 2014/0091811 A1 | 4/2014 | Potyrailo et al. | |
| 2014/0228666 A1* | 8/2014 | Ausin Sanchez | A61B 5/6831 |
| | | | 600/384 |
| 2014/0276186 A1* | 9/2014 | Stanslaski | A61B 5/7225 |
| | | | 600/544 |
| 2015/0065908 A1 | 3/2015 | Kim | |
| 2015/0342497 A1* | 12/2015 | Maktura | A61B 5/0536 |
| | | | 600/547 |

FOREIGN PATENT DOCUMENTS

| | | |
|---|---|---|
| WO | 2007121756 | 11/2007 |
| WO | 2011006014 A1 | 1/2011 |

OTHER PUBLICATIONS

International Search Report and Written Opinion—PCT/US2016/037264—ISA/EPO—dated Aug. 25, 2016.
S. Long, *Mixer Lectures*, Apr. 9, 2009.
Annex C, *Instruments for electrical bioimpedence measurements*, p. 187-216.
M. Min, *Synchronous Sampling and Demodulation in an Instrument for Multifrequency Bioimpedence Measurement*, IEEE Transactions on Instrumentation and Measurement, vol. 56, No. 4, Aug. 2007.
W. Kester, Section 5, *Undersampling Applications*, p. 1-9.
Texas Instruments, *Why Oversample when Undersampling can do the job?*, Application Report, Jun. 2013—Revised Jul. 2013.
Intermediate Frequency (IF) Signal At 72.5MHz (2MHz) Is Aliased Between DC and 5MHz By Sampling At 10MSPS.
International Preliminary Report on Patentability—PCT/US2016/037264—ISA/EPO—dated Oct. 27, 2017.

* cited by examiner

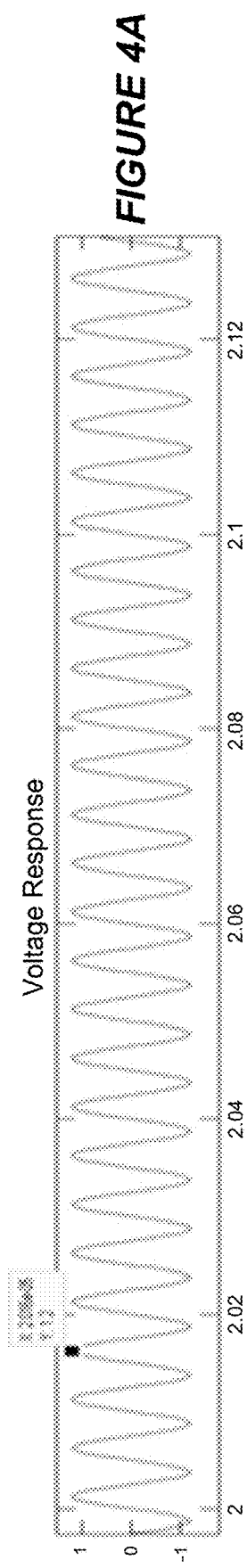
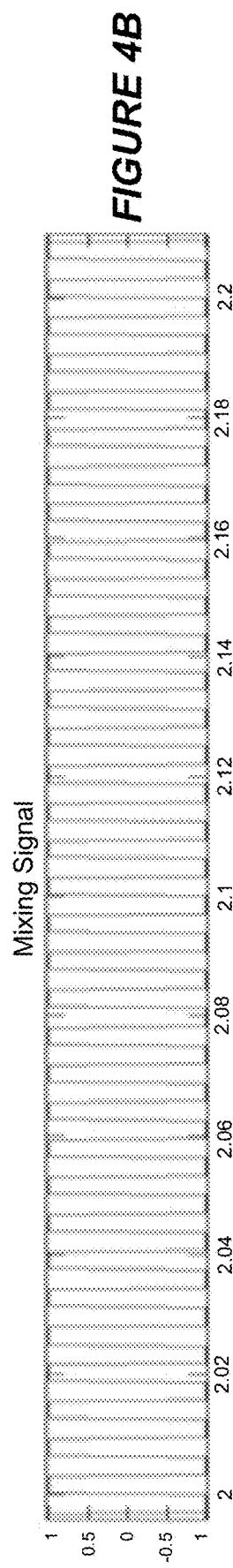
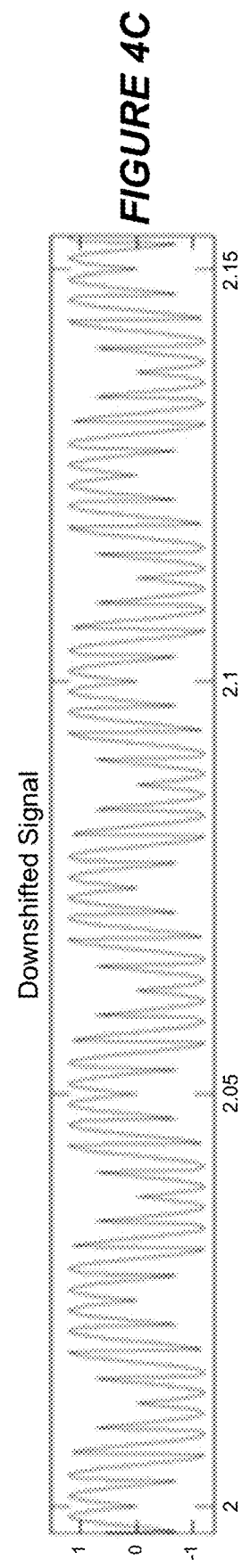
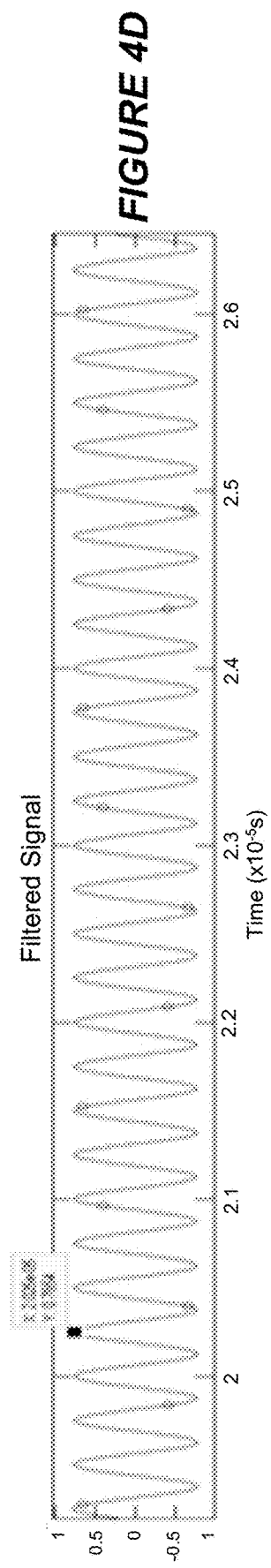

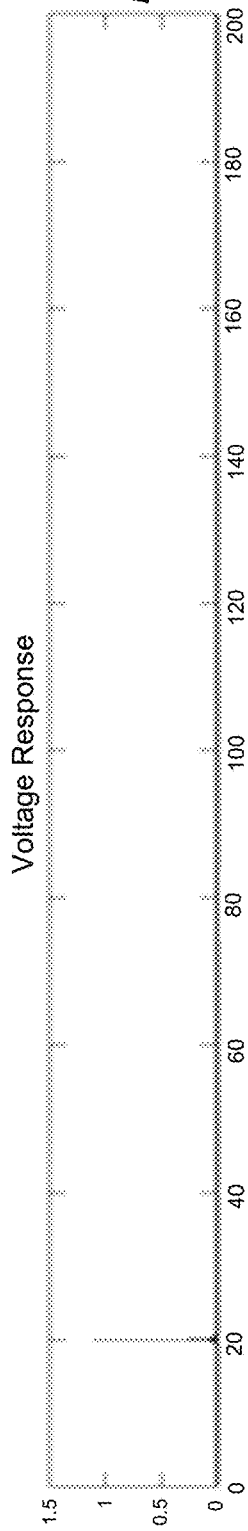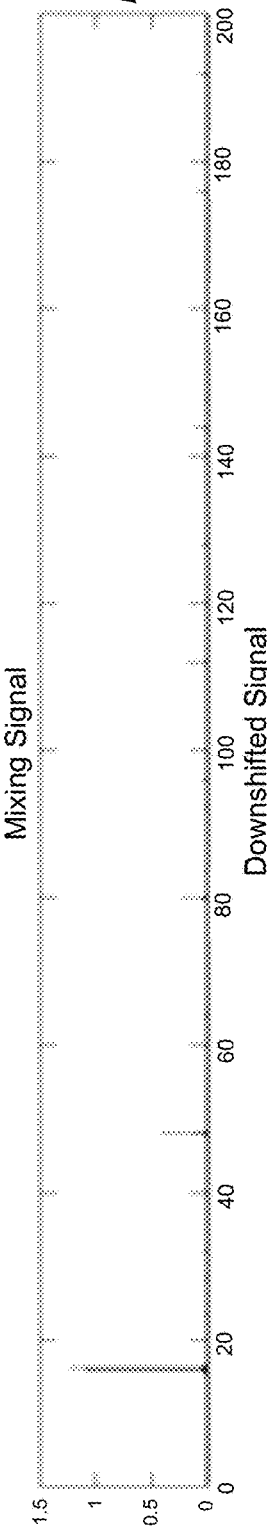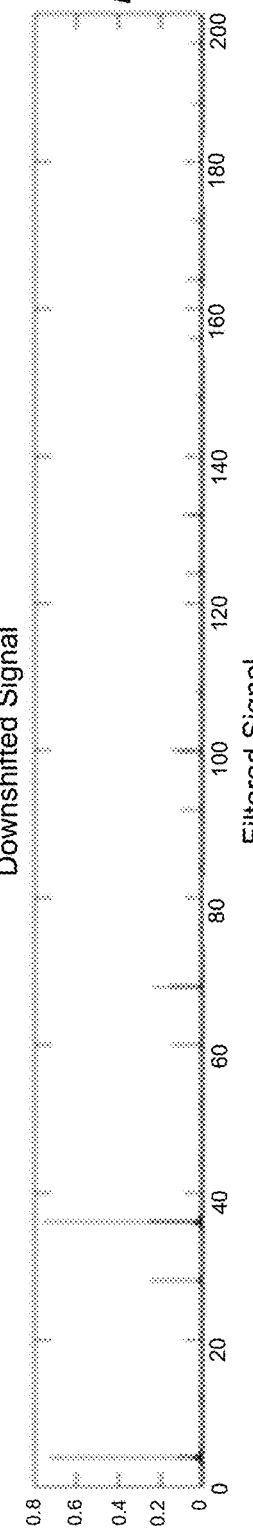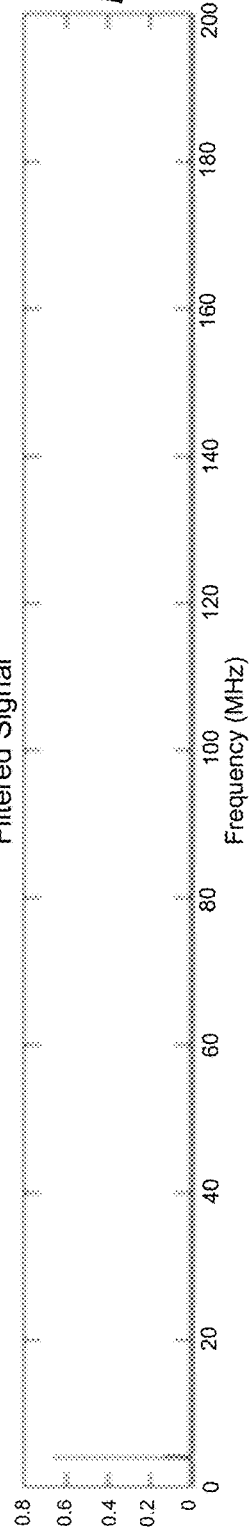

METHODS AND DEVICES FOR RECOVERING DATA FROM AN AMPLITUDE-MODULATED SIGNAL

TECHNICAL FIELD

This disclosure relates generally to sensing devices, and more particularly, to low-power, robust impedance sensing devices.

BACKGROUND

Impedance sensors have been used in various scientific and diagnostic fields to characterize materials as well as to monitor the temporal evolutions of such materials in relation to environmental conditions. Impedance sensors also have recently been contemplated for use in a number of biological applications. A bioimpedance sensor can broadly be characterized as a device that senses or monitors various biological characteristics by exploiting the different electrical properties, and more particularly the different impedances, of various biological tissues. External bioimpedance sensors typically include two or more electrodes that are placed in proximity to, or in contact with, a region of interest on a biological object. A bioimpedance sensor generally functions by introducing an electrical signal into the underlying tissues via a first set of electrodes and detecting a voltage response via a second set of electrodes. The detected voltage response is influenced by the different, and in some instances time-varying, electrical properties of the various tissues through which the injected signal is passed. The voltage response can be analyzed to attempt to determine the biological characteristics of interest.

Bioimpedance sensors are being investigated for use in a number of applications, including monitoring blood pressure, partly as a result of the limitations in the accuracy or portability of traditional measuring devices. For example, a sphygmomanometer is an example of a traditional blood pressure monitoring device that utilizes an inflatable cuff to apply pressure to a region of interest (for example, around an upper arm of the subject). The pressure exerted by the inflatable cuff is designed to restrict arterial flow in order to provide a measurement of systolic and diastolic pressure. Such traditional sphygmomanometers inherently affect the physiological state of the subject which can introduce an error in the blood pressure measurements. Such sphygmomanometers also can affect the psychological state of the subject, which can manifest itself in a physiological state change, and thus, introduce an error in the blood pressure measurements. For example, such devices are often used primarily on isolated occasions, for example, when a subject visits a doctor's office or is being treated in a hospital setting. Naturally, some subjects experience anxiety during such occasions, and this anxiety can influence (for example, increase) the user's blood pressure as well as heart rate.

Additionally, such traditional sphygmomanometers are not portable in the sense that they cannot be worn without restriction of ambulatory movement, or are otherwise inhibiting, interfering or distracting. For these and other reasons, such devices do not provide an accurate estimation or picture of blood pressure, and a user's health in general, over time. While implanted or otherwise invasive devices may provide better estimates of blood pressure over time, such invasive devices generally involve greater risk than noninvasive devices and are generally not suitable for ambulatory use.

SUMMARY

The systems, methods and devices of this disclosure each have several aspects, no single one of which is solely responsible for the desirable attributes disclosed herein.

One aspect of the subject matter described in this disclosure can be implemented in a device for recovering data from an amplitude-modulated signal. The device includes a sensing circuit operable to sense an amplitude-modulated signal having a carrier frequency. In some implementations, the amplitude-modulated signal also is phase-modulated. The device also includes a mixer operable to mix the amplitude-modulated signal with a mixing signal having a mixing frequency to provide a frequency-downshifted signal having an intermediate frequency less than the carrier frequency. The device also includes a filter operable to filter the frequency-downshifted signal to provide a filtered signal. The device further includes a sampler operable to undersample the filtered signal at an undersampling frequency to provide a digital signal, the digital signal being representative of a modulating signal.

The device can further include at least one first electrode operable to receive the amplitude-modulated signal and to pass the amplitude-modulated signal to the sensing circuit. In some implementations, the at least one first electrode can be adapted to couple with a biological object. The device also can include at least one second electrode adapted to couple with the biological object. The device can further include an excitation signal generator operable to generate an excitation signal at the carrier frequency, the at least one second electrode being adapted to provide the excitation signal to the biological object, the amplitude-modulated signal being representative of a response of the biological object to the excitation signal. In some implementations, the modulating signal is representative of an impedance of the biological object. In some implementations, the carrier frequency is greater than or equal to approximately 1 MHz. In some implementations, the excitation signal includes an electrical current signal, and the amplitude-modulated signal includes an electrical voltage signal representative of a voltage response of the biological object to the excitation signal based on the impedance. In some other implementations, the excitation signal includes an electrical voltage signal, and the amplitude-modulated signal includes an electrical current signal representative of a current response of the biological object to the excitation signal based on the impedance.

In some implementations, the device includes a power source and a wearable housing that at least partially encompasses the sensing circuit, the mixer, the filter, the sampler and the power source. In some such implementations, the device further includes a coupling mechanism adapted to couple the wearable housing to a user.

In some implementations, the undersampling frequency is greater than twice the bandwidth of the filtered signal. In some implementations, the device further includes a controller. In some such implementations, the filter includes a bandpass filter having a fixed passband, and the controller sets the mixing frequency of the mixing signal such that the intermediate frequency is substantially equal to a center frequency of the fixed passband of the bandpass filter. In some implementations, the intermediate frequency is greater than a frequency of the modulating signal. In some implementations, the controller also is operable to set the carrier frequency. In some implementations, the filter includes a passive filter. In some implementations, the mixer includes a switching device. In some implementations, the switching device includes a single pole, single throw (SPST) switch or a single pole, double throw (SPDT) switch. In some implementations, the mixing signal is a square wave signal.

Another aspect of the subject matter described in this disclosure can be implemented in a method for recovering data from an amplitude-modulated signal. The method includes sensing an amplitude-modulated signal having a carrier frequency. The method also includes mixing the amplitude-modulated signal with a mixing signal having a mixing frequency to provide a frequency-downshifted signal having an intermediate frequency less than the carrier frequency. The method additionally includes filtering the frequency-downshifted signal to provide a filtered signal. The method further includes undersampling the filtered signal at an undersampling frequency to provide a digital signal, the digital signal being representative of a modulating signal.

In some implementations, the method further includes generating an excitation signal at the carrier frequency, and providing the excitation signal to a biological object. In some such implementations, the amplitude-modulated signal is representative of a response of the biological object to the excitation signal. In some such implementations, the modulating signal is representative of an impedance of the biological object. In some implementations, the carrier frequency is greater than or equal to approximately 1 MHz. In some such implementations, the excitation signal includes an electrical current signal, and the amplitude-modulated signal includes an electrical voltage signal representative of a voltage response of the biological object to the excitation signal based on the impedance.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 4A shows a time domain representation of an example excitation signal $I_{Excit}$ having an excitation frequency $f_{Excit}$ of 20 MHz.

FIG. 4B shows a time domain representation of an example square-wave mixing signal $V_{Mix}$ having a switching frequency $f_{Switch}$ of 16 MHz.

FIG. 4C shows a time domain representation of an example frequency-downshifted signal $V_{Int}$ having an intermediate frequency $f_{Int}$ of 4 MHz.

FIG. 4D shows a time domain representation of an example filtered signal $V_{Filter}$ having an intermediate frequency $f_{Int}$ of 4 MHz.

FIG. 5A shows a frequency domain representation of the example excitation signal $I_{Excit}$ of FIG. 4A.

FIG. 5B shows a frequency domain representation of the example square-wave mixing signal $V_{Mix}$ of FIG. 4B.

FIG. 5C shows a frequency domain representation of the example frequency-downshifted signal $V_{Int}$ of FIG. 4C.

FIG. 5D shows a frequency domain representation of the example filtered signal $V_{Filter}$ of FIG. 4D.

Like reference numbers and designations in the various drawings indicate like elements.

DETAILED DESCRIPTION

Figure 1:
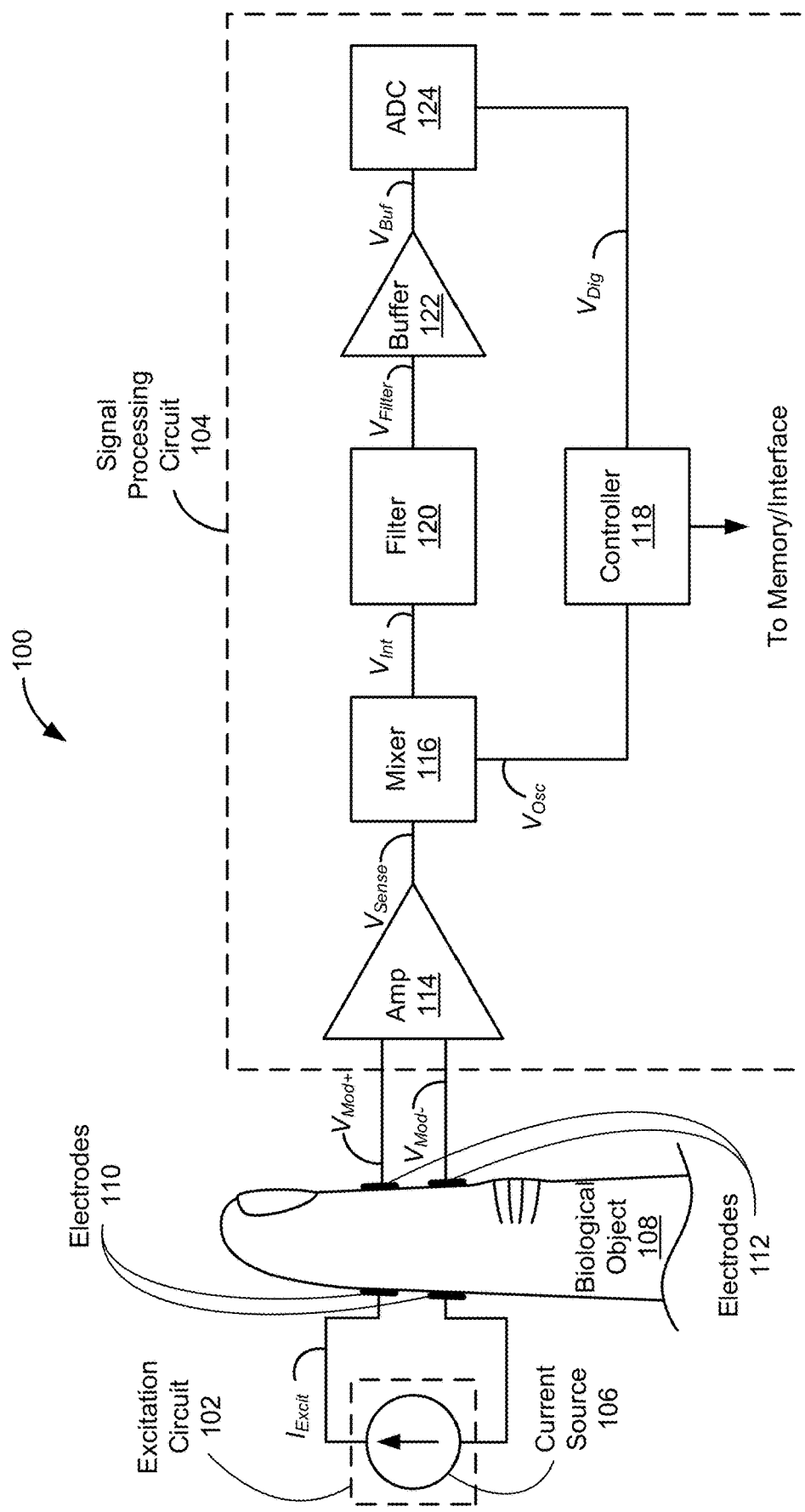
FIG. 1 shows a circuit diagram of an example bioimpedance sensor according to some implementations.

The following description is directed to certain implementations for the purposes of describing various aspects of this disclosure. However, a person having ordinary skill in the art will readily recognize that the teachings herein can be applied in a multitude of different ways. The described implementations may be implemented in any device, apparatus, or system that is capable of receiving an electrical signal and performing signal processing on the received signal. Some of the concepts and examples provided in this disclosure are especially applicable to bioimpedance sensing applications. However, some implementations also may be applicable to other types of biological sensing applications. Thus, the teachings are not intended to be limited to the implementations depicted solely in the Figures, but instead have wide applicability as will be readily apparent to one having ordinary skill in the art.

As used herein, the conjunction "or" is intended herein in the inclusive sense where appropriate unless otherwise indicated; that is, the phrase "A, B or C" is intended to include the possibilities of A, B, C, A and B, B and C, A and C and A, B and C. Additionally, a phrase referring to "at least one of" a list of items refers to any combination of those items, including single members. As an example, "at least one of: A, B, or C" is intended to cover: A, B, C, A-B, A-C, B-C, and A-B-C.

Various implementations relate generally to a signal processing circuit for use in impedance sensing applications. Some implementations more specifically relate to a low-power, wearable and robust signal processing circuit for a bioimpedance sensor. Some implementations also relate to a signal processing circuit operable to undersample a voltage response signal detected after passing an excitation signal through a biological object. Some implementations also relate to a signal processing circuit that includes a mixer operable to downshift a frequency of the detected voltage response signal from a carrier frequency to an intermediate frequency. In some implementations, such frequency-downshifting capabilities enable the signal processing circuit to position the intermediate frequency at a center frequency of a bandpass filter. In some implementations, such frequency-downshifting enables the use of any excitation signal frequency. In point of fact, some implementations more specifically relate to a high excitation frequency bioimpedance sensor. Some implementations also relate to a broadband bioimpedance sensor capable of generating multiple excitation frequencies.

Particular implementations of the subject matter described in this disclosure can be implemented to realize one or more of the following potential advantages. Some implementations of the bioimpedance sensors described herein are designed to consume relatively little power enabling continuous wearing and monitoring of a biological property, characteristic or signal of interest over extended periods of time (for example, days, weeks or even a month or more) without recharging or other interruption. Some implementations of the bioimpedance sensors described herein also are designed with small form factors and within housings that can be coupled to a user so as to be wearable, non-invasive, and non-restrictive of ambulatory use. Not only do such devices not interfere with the user's daily or other desired activities, they also encourage continuous wearing by virtue of such non-interference.

The bioimpedance sensors described herein can generally be operable to measure one or more of a variety of biological properties, characteristics or signals (hereinafter collectively referred to as "characteristics"). In various applications, such characteristics can include periodic time-varying characteristics, aperiodic time-varying characteristics as well as characteristics that are relatively constant over time. Some implementations are especially applicable to measuring (also referred to herein as "sensing," "detecting," "monitoring" or "determining") one or more of a number of cardiovascular characteristics such as heartrate, blood pressure, pulse shape, and pulse wave velocity. Generally, various tissues such as blood, skin, muscle, fat, tendons, ligaments, bone and lymph have different impedance properties. Additionally, the impedance properties of some tissues, such as blood, can vary periodically or aperiodically over both short-term and long-term time durations. The different impedance properties of the tissues in a region of interest can be exploited by the bioimpedance sensors and signal processing circuits described herein to measure the biological characteristics of interest.

Electrical impedance (typically symbolized as Z) can generally be defined as a measure of a medium's opposition to current flow responsive to an applied voltage. By way of background, a medium's impedance is generally a complex number; that is, the impedance includes both a real part and an imaginary part. The real part of the impedance is referred to as the electrical resistance (R), while the imaginary part is referred to as the reactance (X). The reactance contribution to the impedance of a medium arises from the inductive and capacitive properties of the medium in the presence of an alternating current (AC) electrical field. Also by way of background, a medium's admittance (Y) is defined as the inverse of the medium's impedance. As such, the admittance also is a complex number including a real part, referred to as the conductance (G), as well as an imaginary part, referred to as the susceptance (B). As with the reactance, the susceptance contribution to the admittance of a medium arises from the inductive and capacitive properties of the medium in the presence of an AC electric field. The susceptance of a medium also is directly related to the permittivity ($\varepsilon$) of the medium, which can be characterized as the medium's ability to resist an electric field.

In some implementations, for example, when measuring blood pressure, heartrate or other cardiovascular characteristics, the dynamic properties of arteries are of particular interest. In some more specific applications, the fluctuating changes in the cross-sections of the arteries synchronous with a user's heartbeat are of particular interest. The blood in the arteries has a greater electrical conductivity (and generally a greater admittance) than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. During the portion of the cardiac cycle in which the left ventricle of the heart pumps blood into the arteries ("ventricular systole") the blood pressure in the arteries increases (to a maximum "systolic pressure") resulting in the expansion of the arterial cross-sections. As a result of the increase in blood in the arteries, the electrical conductivity (and more generally the admittance) of the region of interest increases (and correspondingly, the impedance decreases). Similarly, during the portion of the cardiac cycle in which the left ventricle of the heart is relaxing and filling with blood ("ventricular diastole") the blood pressure in the arteries decreases (to a minimum "diastolic pressure") resulting in the contraction of the arterial cross-sections. As a result of the decrease in blood in the arteries, the resistance (and more generally the impedance) of the region of interest increases (and correspondingly, the admittance decreases).

The bioimpedance sensors described herein generally function by applying an electrical excitation signal to a region of interest via two or more input electrodes, and detecting an output signal (or output signals) via two or more output electrodes. As described above, in cardiovascular applications especially, the region of interest generally includes a number of arteries. In some more specific implementations described herein, the electrical excitation signal is a current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance of the underlying arteries, which fluctuates synchronously with the user's heartbeat as described above.

Additionally, while the time-varying conductivities of the arteries (or other tissues) in the region of interest typically account for a dominant role in the amplitude modulation of the detected voltage signal, the time-varying permittivities of the arteries (and other tissues) also can play a non-trivial role in the amplitude modulation. This is generally because these tissues, including blood, generally have resistive as well as capacitive properties (some tissues also can have inductive properties, but such inductive properties typically have a negligible effect on the modulation). Additionally, because the permittivity of the underlying arteries also can vary synchronously with the user's heartbeat, the detected voltage response signal also can be phase-modulated based on the permittivity of the underlying arteries (as can be observed by a phase shift in the detected voltage response signal relative to the excitation signal). The characteristics of the amplitude and phase modulation of the detected voltage response signal can be processed to provide indications of the user's heartrate, systolic and diastolic blood pressure, or other cardiovascular characteristics of the user over time.

In some applications, the roles of the permittivities and conductivities in affecting the impedance of a given tissue also are generally dependent on the frequency of the excitation signal. As such, in various implementations, the frequency of the excitation signal is selected based on the electrical properties of the tissues in the region of interest. For example, in some cardiovascular applications, the excitation frequency is selected to provide sufficient amplitude modulation by the blood in the arteries. In some such implementations, the excitation frequency also can be selected to minimize interference or noise caused by other tissues in the region of interest such as, for example, skin, fat, lymph, muscles, tendons, ligaments and bone.

As described above, the detected voltage signal is representative of the voltage response of the tissues in the region of interest to the applied excitation signal. As a result, the detected voltage response signal includes an excitation frequency component (at the excitation frequency) that is amplitude-modulated, and generally also phase-modulated, by the biological tissues in the region of interest. To determine various biological characteristics, information in the detected voltage response signal is generally demodulated from the excitation frequency component. Some existing signal processing circuits in bioimpedance sensing devices utilize analog demodulators to demodulate the detected voltage response signal. Some such analog demodulators utilize an analog mixer, such as an analog multiplier, to mix the detected voltage response signal with two other signals: a first signal (typically referred to as the "I channel") that is in-phase with the excitation signal and a second signal (typically referred to as the "Q channel") that is in quadrature-phase with the excitation signal. However, such analog multipliers or mixers are high-power-consuming devices and thus, generally unsuitable or undesirable for long-term wearable use applications.

Some other bioimpedance sensors avoid such analog multipliers or mixers, and instead utilize digital mixing. However, in existing bioimpedance sensors utilizing digital mixing, the detected signal must be sampled at a very high sampling frequency to satisfy the Nyquist sampling criterion to avoid aliasing. The Nyquist sampling criterion requires that the sampling frequency $f_S$ at which the detected signal is sampled be greater than twice the highest frequency in the detected signal. But high frequency sampling traditionally requires a fast, high-resolution analog-to-digital converter (ADC) to obtain the precision needed at high-sampling frequencies. Fast, high-resolution ADCs are relatively expensive and also are high-power-consuming devices making them unsuitable or undesirable for long-term wearable use applications. Additionally, if frequency-downshifting to a zero frequency carrier signal is applied, both an I channel and a Q channel also are needed. Such sensors also are known to be susceptible to pink (1/f) noise and also to drift.

Some other bioimpedance sensors utilize undersampling. While undersampling inherently violates the Nyquist sampling criterion, undersampling can still enable a reconstruction of the detected signal if the sampling frequency fulfills the Shannon sampling criterion. The Shannon sampling criterion requires that the sampling frequency $f_S$ be greater than twice the bandwidth BW of the sampled signal ($f_S > 2BW$). Typically, such devices require a very narrow bandpass filter to filter the detected signal before it is sampled by the ADC to avoid aliasing of signals outside of a band of width 2BW. For example, the bandpass filter should filter out frequency components above the sampling frequency $f_S$. However, such existing undersampling devices also are susceptible to DC offsets and drifting, which can render the devices inoperable or ineffective. For example, DC offset and drifting can place the frequency of the detected analog signal outside of the bandpass filter's passband and bring undesired frequency components that should be filtered out (such as aliases) into the passband. Some bioimpedance sensors that utilize undersampling attempt to accommodate for such DC offsets or drifting artifacts by adjusting the center frequency of the narrow bandpass filter. However, adjustable narrow bandpass filters are challenging to design. Furthermore, adjustable narrow bandpass filters are typically implemented with analog filters. Such analog filters also are high-power-consuming devices generally making them unsuitable or undesirable for long-term wearable use applications. Digital filtering can additionally or alternatively be utilized, however, digital filtering generally requires a relatively powerful processor. Such processors also consume a substantial amount of power. Additionally, in broadband multi-frequency excitation applications (required or desirable for certain biological characteristic measurements), the problem is exacerbated because different excitation frequencies are present, whether simultaneously or in alternating fashion. Such applications generally require multiple adjustable narrow bandpass filters having different center frequencies.

As is evident from the foregoing examples, existing designs have yet to achieve a bioimpedance sensor that is truly and practically wearable by a user. As described above, the high analog-to-digital resolution necessary in some existing bioimpedance sensors to obtain reliable and precise measurements of the biological characteristics of interest has traditionally necessitated power consumption higher than what is acceptable for a long-term wearable device. Additionally, the broadband flexibility necessary or desirable to obtain reliable and precise measurements for a variety of biological characteristics of interest also has been unattainable in a long-term wearable device.

Various implementations described herein relate generally to a signal processing circuit for use in a low-power, wearable bioimpedance sensor (also referred to herein as a "sensing device"). In some implementations, the signal processing circuit is operable to undersample a detected voltage response signal while enabling full recovery (or "reconstruction") of the data of interest. In some implementations, the signal processing circuit includes a mixer operable to downshift a carrier frequency of the detected voltage response signal from the excitation frequency to an intermediate frequency. In some implementations, such frequency-downshifting capabilities enable the signal processing circuit to position the frequency of the voltage response signal at a center frequency of a bandpass filter having a fixed passband. This is in contrast to designs in which the center frequency of an adjustable bandpass filter is adjusted to accommodate the carrier frequency of the detected voltage response signal. Advantageously, frequency-downshifting enables the use of virtually any desirable excitation signal frequency, as well as the use of multiple excitation frequencies for broadband applications.

In some implementations, the signal processing circuit can be adapted and operable to monitor a user's heartrate, blood pressure, pulse shape, and pulse wave velocity, among other cardiovascular characteristics. Additionally or alternatively, the signal processing circuit can be adapted and operable to determine, or provide data usable to determine, other biological characteristics such as, for example, body water index or tissue composition. In some implementations, the signal processing circuit can additionally or alternatively be adapted and operable to monitor activity data, for example, data indicative of motion of the user (for example, during exercise as well as during the user's normal daily or weekly routines). The signal processing circuit also can be used to facilitate various medical imaging applications. To achieve these and other goals, the bioimpedance sensor, and the signal processing circuit within it, is designed for low-power consumption while enabling the use of high excitation frequencies (for example, up to or greater than 1 MHz, and in some applications, up to or exceeding 20 MHz). The signal processing circuit also is designed to have the broadband flexibility needed or desirable for accurate and reliable measurements and processing of a variety of biological characteristics of interest.

In some implementations, the bioimpedance sensor, and the signal processing circuit within it, is incorporated within a wearable housing. In some specific implementations, the wearable housing includes (or is connected with) a physical coupling mechanism for removable attachment to the user. The housing can be formed using any of a variety of suitable manufacturing processes, including injection molding and vacuum forming. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, the wearable bioimpedance sensor is both non-invasive and not physically-inhibiting. As such, the bioimpedance sensor enables long-term wearing and monitoring (for example, over days, weeks or a month or more without interruption) of one or more biological characteristics of interest to obtain a better picture of such characteristics over time, and generally, a better picture of the user's health.

FIG. 1 shows a circuit diagram of an example bioimpedance sensor 100 according to some implementations. The bioimpedance sensor 100 includes an excitation circuit 102 and a signal processing circuit 104. The excitation circuit 102 includes an excitation signal generator 106 for generating an electrical excitation signal $I_{Excit}$ having an adjustable excitation frequency $f_{Excit}$. As described above, in some implementations, the excitation signal generator 106 can simultaneously or alternately generate multiple excitation signals at different excitation frequencies depending on the biological characteristics of interest. In the illustrated implementation, the excitation signal generator 106 functions as a current source that provides the excitation signal $I_{Excit}$ in the form of an electrical current signal, and more specifically, a radio frequency (RF) alternating current (AC) signal. In some implementations, the excitation signal generator 106 can include a current mirror comprised of a multiple MOSFETs or bipolar junction transistors as well as other circuit components such as amplifiers.

The excitation signal $I_{Excit}$ is injected into (or "provided to") a region of interest of a biological object 108 via a pair of input electrodes 110 in contact with the biological object 108. In the illustrated example, the biological object 108 is a human finger and the bioimpedance sensor 100 is positioned on or around, or otherwise coupled with, a portion of the human finger. The injected excitation signal $I_{Excit}$ can be a single-ended signal or a differential signal. The bioimpedance sensor 100 also includes a pair of output electrodes 112 in contact with the region of interest of the biological object 108. The output electrodes 112 are operable to sense an amplitude- and phase-modulated voltage response signal $V_{Mod}$. The voltage response signal $V_{Mod}$ includes the data of interest resulting from the effects of the differing and in some instances time-varying impedances of the tissues in the region of interest.

While the input electrodes 110 and the output electrodes 112 are positioned on opposing sides, respectively, of the biological object 108 in FIG. 1, in some other implementations, the input electrodes 110 and the output electrodes 112 can be positioned proximate to or adjacent one another on a surface of a region of interest of the biological object 108. In some specific implementations, the two input electrodes 110 and the two output electrodes 112 are arranged in a tetrapolar configuration. Generally, the input electrodes 110 and the output electrodes 112 can be positioned in contact with any desired region of interest of a biological object 108. For example, in some other implementations, the bioimpedance sensor 100 and the input and output electrodes 110 and 112, respectively, can be positioned around a wrist of a user. In some such implementations, the bioimpedance sensor can be enclosed in a housing that resembles a watch or wrist band having a strap or band that connects around the wrist to keep the bioimpedance sensor in place, and specifically, such that the input electrodes 110 and the output electrodes 112 are in contact with the skin of the user. In some other implementations, the bioimpedance sensor 100 can similarly be positioned around a forearm, an upper arm, an ankle, a lower leg, an upper leg, or a torso (for example, around a user's chest and upper back) using a strap or band. In some other implementations, the bioimpedance sensor 100 can be positioned on a region of interest of the user without the use of a strap or band. For example, the bioimpedance sensor 100 can be enclosed in a housing that is secured to the skin of a region of interest of the user using an adhesive or other suitable attachment mechanism.

Additionally, while the implementation described with reference to FIG. 1 includes two input electrodes 110 and two output electrodes 112, in some other implementations, the bioimpedance sensor 100 can include any desirable number of input electrodes 110 and any desirable number of output electrodes 112. The two sets of electrodes may be identical or different, and in some implementations, have one or more electrodes in common. For example, the bioimpedance sensor 100 can include a single dedicated input electrode 110 for injecting the excitation signal $I_{Excit}$, a single dedicated output electrode 112 for detecting the amplitude- and phase-modulated voltage response signal $V_{Mod}$, and a shared common electrode (for example, a shared ground electrode). In other implementations, it can be advantageous to include two (or more) input electrodes 110 and two (or more) output electrodes 112. Using two or more input electrodes 110 and two or more output electrodes can better confine the measuring region of interest so that a larger amplitude voltage response signal $V_{Mod}$ is obtained as compared with configurations in which only a single input electrode and a single output electrode are used. Using two or more input electrodes 110 and two or more output electrodes 112 also reduces interference from other tissues as compared with single input and single output electrode (or "two-pole") configurations.

As described above, the detected voltage response signal $V_{Mod}$ is representative of the voltage response of the tissues in the region of interest to the applied excitation signal. As a result, the detected voltage response signal $V_{Mod}$ includes the data to be used in determining the biological characteristics of interest. This data is "carried" at the excitation frequency $f_{Excit}$ in the form of the amplitude modulation, and in some instances phase modulation, of the detected voltage response signal $V_{Mod}$ caused by the time-varying impedance of the biological tissues in the region of interest. It is the amplitude modulation that determines the envelope of the waveform of the voltage response signal $V_{Mod}$.

In some implementations, the term "modulating signal" refers to a signal representative of a time-varying impedance, for example, a time-varying impedance of the biological object 108. In such implementations, it is the time-varying impedance that is the physical cause of the amplitude and phase modulation observed in the detected voltage response signal $V_{Mod}$. In some implementations, it is the modulating signal that can be reconstructed by the signal processing circuit 104. In some applications, the modulating signal is indicative of a biological signal. For example, in the case of an arterial distension signal, the time-varying arterial distension synchronous with a heartbeat can be the physical cause of the time-varying impedance, and in such case, the modulating signal can be representative of the arterial distension signal and have a modulating frequency equal to a frequency of the heartbeat. Continuing this example, the biological characteristics of interest can include the arterial distension signal itself or various properties or data that can be extracted from the arterial distension signal, for example, such as heartrate and blood pressure among other characteristics. However, it is to be understood that the term "signal" is not limited to periodic time-varying data in all implementations; rather, the term signal also is applied inclusively to include aperiodic time-varying data as well as data that remains relatively constant over time.

Figure 2A:
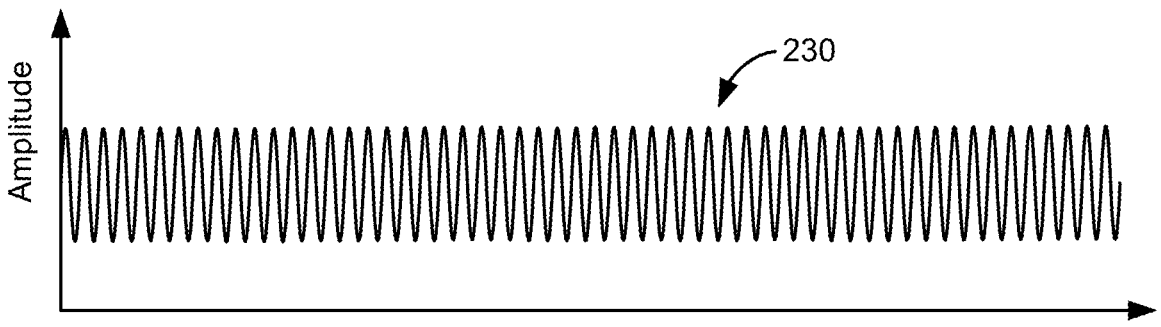
FIG. 2A shows a time-domain representation of a fictional excitation signal $I_{Excit}$ having an excitation frequency $f_{Excit}$.
Figure 2B:
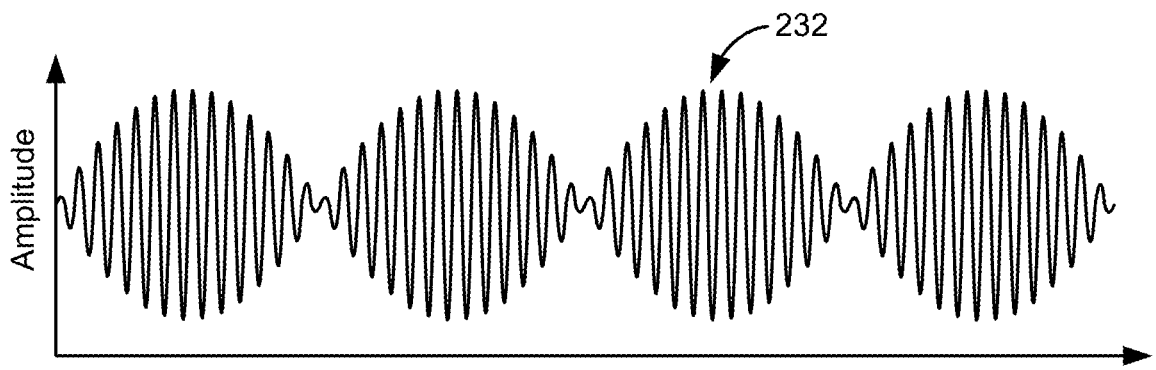
FIG. 2B shows an example time-domain representation of a fictional voltage response signal $V_{Mod}$ also having the excitation frequency $f_{Excit}$.
Figure 2C:
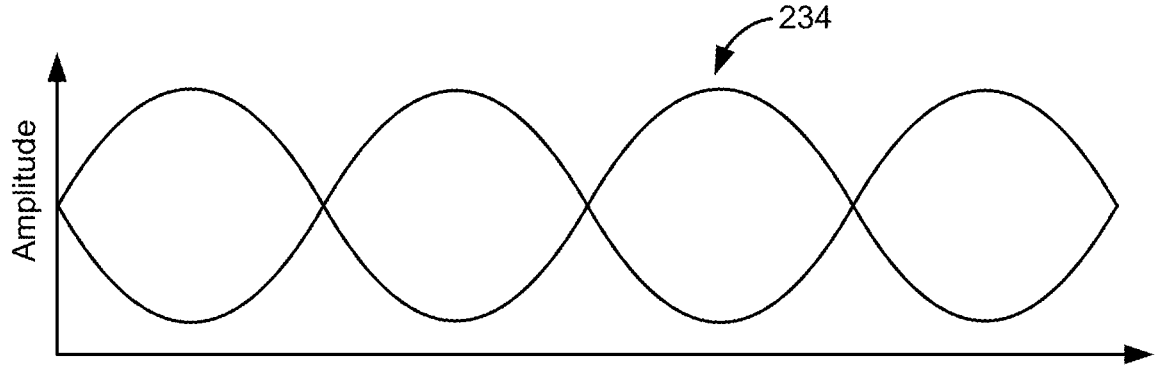
FIG. 2C shows a representation of the envelope of the waveform of the voltage response signal $V_{Mod}$ of FIG. 2B.

For didactic purposes, FIG. 2A shows a time-domain representation of a fictional excitation signal $I_{Excit}$ 230 having an excitation frequency $f_{Excit}$. FIG. 2B shows an example time-domain representation of a fictional voltage response signal $V_{Mod}$ 232 also having the excitation frequency $f_{Excit}$. As shown in FIG. 2B, the voltage response signal $V_{Mod}$ is amplitude-modulated by the medium into which the excitation signal $I_{Excit}$ 230 is provided. The amplitude modulation defines the envelope of the waveform of the voltage response signal $V_{Mod}$. FIG. 2C shows a representation of the envelope 234 of the waveform of the voltage response signal $V_{Mod}$ of FIG. 2B. In the didactic example shown, the amplitude modulation, and thus the envelope 234 of the waveform, is periodic. However, there is no requirement that the amplitude modulation be periodic. To be clear, in FIGS. 2A-2C, the signals and frequencies shown are didactic in nature: used to illustrate the concept of amplitude modulation and not to limit the signals and frequencies used in actual implementations of the bioimpedance sensors described herein.

Figure 3:
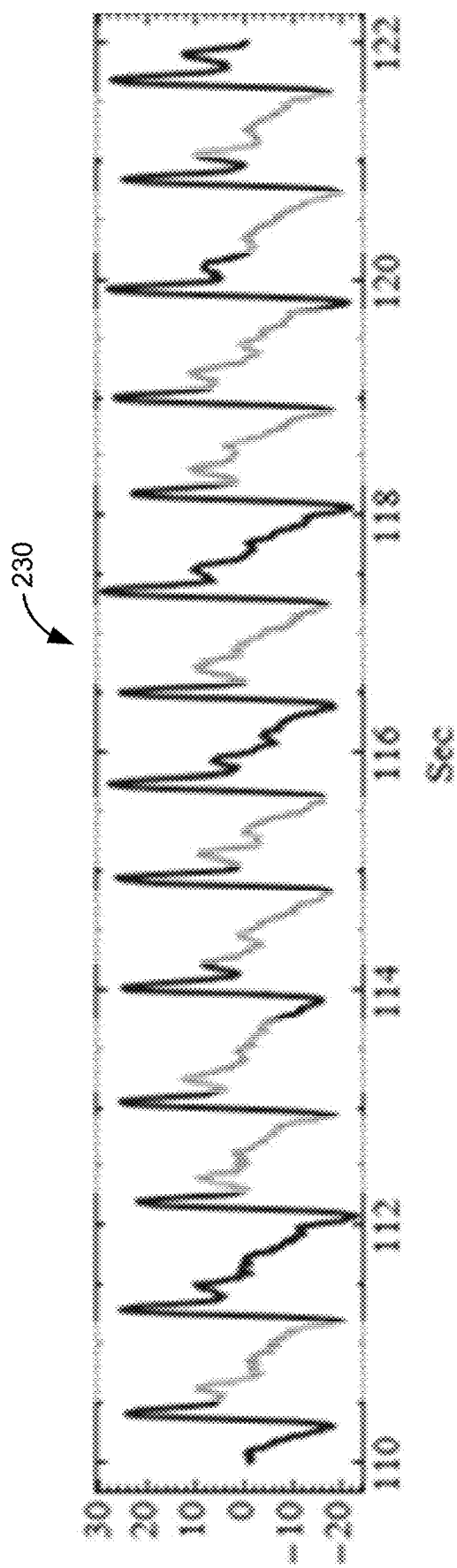
FIG. 3 shows an example of an arterial distension signal.

In implementations in which the bioimpedance sensor 100 is operable for use in determining blood pressure or heartrate, the time-varying impedance caused by the fluctuating arterial cross-sections (the "arterial distension signal") synchronous with the user's heartbeat can be of particular interest. FIG. 3 shows an example of an arterial distention signal 336. The horizontal axis is measured in seconds. The vertical axis (the amplitude) is measured in normalized units of resistance (for example, mili-Ohms).

In describing the signal processing circuit 104 of FIG. 1, reference will be made to the example signals shown in FIGS. 4A-4D and the respective frequency responses shown in FIGS. 5A-5D. However, the signals and frequencies shown and described with references to FIGS. 4A-4D and 5A-5D are not to be construed as limiting the signals or frequencies applicable to the disclosed implementations. FIG. 4A shows a time domain representation of an example excitation signal $I_{Excit}$ having an excitation frequency $f_{Excit}$ of 20 MHz. FIG. 5A shows a frequency domain representation of the example excitation signal $I_{Excit}$ of FIG. 4A. As shown in FIG. 5A, the power of the excitation signal $I_{Excit}$ is concentrated at the excitation frequency $f_{Excit}$ of 20 MHz.

As described above, the input electrodes 110 are positioned to inject the excitation signal $I_{Excit}$ into the biological object 108. The output electrodes 112 are positioned to detect the resultant amplitude-modulated voltage response signal $V_{Mod}$. The voltage response signal $V_{Mod}$ detected by the output electrodes 112 is received by the signal processing circuit 104. In differential signal implementations, the voltage response signal $V_{Mod}$ includes a first component detected by a first one of the pair of output electrodes 112 and a second component detected by a second one of the pair of output electrodes. For example, the first component of the voltage response signal $V_{Mod}$ can be a positive component ($V_{Mod+}$) of the voltage response signal $V_{Mod}$ and the second component of the voltage response signal $V_{Mod}$ can be a negative component ($V_{Mod-}$) of the voltage response signal $V_{Mod}$. The first and second components of the voltage response signal $V_{Mod}$ detected by the output electrodes 112 are input to a sensing circuit 114. In single-ended signal implementations, one of the output electrodes 112 is grounded or otherwise at a common voltage while the second one of the output electrodes receives the voltage response signal $V_{Mod}$.

In the illustrated implementation, the sensing circuit 114 includes an amplifier (hereinafter the sensing circuit 114 also is generally referred to as the "amplifier 114"). The first component ($V_{Mod+}$) of the voltage signal $V_{Mod}$ received by the first one of the output electrodes 112 is input to a first ("positive") input of the amplifier 114. The second component ($V_{Mod-}$) of the voltage signal $V_{Mod}$ received by the second one of the output electrodes 112 is input to a second ("negative") input of the amplifier 114. The amplifier 114 detects and amplifies a difference between the first and second components of the voltage signal $V_{Mod}$ to provide a sensed signal $V_{Sense}$. In some specific implementations, the amplifier 114 is an instrumentation amplifier (IA). An IA is a type of differential amplifier that generally includes input buffer amplifiers, for example, one input buffer amplifier to buffer each of the two inputs to a differential amplifier. Using an IA as the amplifier 114 can be advantageous, for example, because the input buffer amplifiers can eliminate the need for input impedance matching, and because IAs characteristically have low DC offset, low drift, low noise, high open-loop gain, high common-mode rejection ratio, and high input impedances. As such, an IA provides high accuracy and stability. In some implementations in which the amplifier 114 is an IA, the IA includes three operational amplifiers (op-amps), one op-amp to implement each of the input buffers, and one op-amp to sense and amplify a difference between the signals produced by the input buffers to produce the sensed signal $V_{Sense}$. In some other implementations, the amplifier 114 can be another type of differential amplifier, another combination of one or more op-amps, or another suitable sensing circuit or device.

The sensed signal $V_{Sense}$ is then processed through a mixer 116. The mixer 116 can be controlled by a controller 118, and in some specific implementations, a low-power controller such as a field-programmable gate array (FPGA) or a microcontroller. In some implementations, the same controller 118 also can be used to control the excitation circuit 102, and specifically, to control or adjust the excitation frequency (or frequencies) $f_{Excit}$ of the excitation signal $I_{Excit}$. In various implementations, the mixer 116 functions to downshift the carrier frequency of the sensed signal $V_{Sense}$ from the excitation frequency $f_{Excit}$ to an intermediate frequency $f_{Int}$ lower than the excitation frequency $f_{Excit}$. In implementations or applications in which the amplitude modulation of the sensed signal $V_{Sense}$ is periodic or quasi-periodic, the intermediate frequency $f_{Int}$ can be a frequency between the excitation frequency $f_{Excit}$ and a frequency of the amplitude modulation (for example, a modulating frequency of a modulating signal such as an arterial distension signal in cardiovascular applications). The output of the mixer 116 is a frequency-downshifted signal $V_{Int}$ having the intermediate frequency $f_{Int}$. As will be described below, the downshifted signal $V_{Int}$ also can include mirrored harmonics of the intermediate frequency $f_{Int}$. But notably, the frequency-downshifted signal $V_{Int}$ still carriers the data of interest in the form of the amplitude and phase modulation.

In some implementations, the mixer 116 can be implemented with a switching circuit that switches between high and low, on and off, or inverting and non-inverting as controlled by the controller 118. In some implementations in which the mixer 116 is implemented as a switching circuit, the mixer 116 toggles from high to low based on an oscillator signal $V_{Osc}$ output from the controller 118 at an oscillation frequency $f_{Osc}$. For example, the controller 118 can include a frequency generator such as a voltage-controlled oscillator (VCO) circuit that generates the oscillator signal $V_{Osc}$ at the oscillation frequency $f_{Osc}$. In some such implementations, the mixing signal $V_{Mix}$ produced by the switching circuit based on the oscillation signal can be a square wave signal at a mixing frequency (also referred to herein as the "switching frequency $f_{Switch}$") equal to the oscillation frequency $f_{Osc}$. In such an example switching circuit implementation, the mixer 116 passes the sensed signal $V_{Sense}$ (or a multiple thereof) when the mixing signal is high and outputs a low value (for example, a reference voltage or ground) when the mixing signal is low. FIG. 4B shows a time domain representation of an example square-wave mixing signal $V_{Mix}$ having a switching frequency $f_{Switch}$ of 16 MHz. FIG. 5B shows a frequency domain representation of the example square-wave mixing signal $V_{Mix}$ of FIG. 4B. As shown in FIG. 5B, the power of the mixing signal $V_{Mix}$ is concentrated at the switching frequency $f_{Switch}$ of 16 MHz.

In some implementations, the mixer 116 can be implemented using a single pole, single throw (SPST) switch, or a single pole, double throw (SPDT) switch. Such switches can have a maximum power consumption on the order of a micro-Watt (μW)—a power consumption that can be 4, 5 or more orders of magnitude less than traditional analog mixers. In implementations in which the mixer 116 includes an SPDT switch, the mixer 116 also may include an inverting amplifier and a summing amplifier. The use of a SPDT switch can eliminate any DC component that otherwise may appear in the frequency-downshifted signal $V_{Int}$. In some other implementations, the mixer 116 can be implemented using a ring mixer, such as a diode-based ring mixer, which can be considered as a special type of SPDT switch. In some other implementations, the mixer 116 can be implemented using one or more high speed transistors, such as one or more MOSFETs.

In some other implementations, the mixer 116 can be an analog switch. In some such implementations, the analog switch can be implemented in CMOS as a pair of MOSFET transistors: the first being an N-channel MOSFET and the other being a P-channel MOSFET. In other implementations, the mixer 116 can be implemented using a multiplier or a multiplicative mixer. However, such multipliers and multiplicative mixers generally can't achieve the low power consumption of a switch, such as the SPST, SPDT or diode-based ring mixer switches described above, and thus, may be less desirable in a long-term wearable sensing device. Additionally, in some other implementations, the mixing signal $V_{Mix}$ is not a square wave signal. For example, if the mixer 116 is implemented as a square law device, the mixing signal $V_{Mix}$ can be advantageously be a sinusoidal signal. However, again, such a square law device generally can't achieve the low power consumption desirable or suitable in a long-term wearable sensing device.

As described above, the output of the mixer 116 is a frequency-downshifted signal $V_{Int}$ having the intermediate frequency $f_{Int}$. In some such implementations, the mixer 116 functions as a multiplier that multiplies the sensed signal $V_{Sense}$ with the mixing signal $V_{Mix}$ to generate the frequency-downshifted signal $V_{Int}$. Mathematically, the multiplication by the mixer 116 corresponds to a convolution of the frequency responses of the two signals $V_{Sense}$ and $V_{Mix}$. Assuming that the sensed signal $V_{Sense}$ is a sinusoid and that the mixing signal $V_{Mix}$ is a square wave, the output of the mixer 116—the frequency-downshifted signal $V_{Int}$—can be determined from equation (1) below:

$$V_{Int} = \frac{V}{2}\cos(2\pi f_{Exc} * t) + \frac{2V}{\pi}[\cos(2\pi f_{Exc} * t)\sin(2\pi f_{Switch} * t) + evenharmonics], \quad (1)$$

where V is the amplitude of the sensed signal $V_{Sense}$ and t represents time. Notably, any excitation frequency (or frequencies) can be selected for the excitation signal $I_{Excit}$ because the switching frequency $f_{Switch}$ can be adjusted by the controller 118 to obtain the desired intermediate frequency $f_{Int}$ of the downshifted signal $V_{Int}$. It is also noted that equation (1) is general to unbalanced mixers; if a balanced mixer is used to implement the mixer 116, the second term (oscillating at the excitation frequency $f_{Excit}$) disappears.

In the frequency domain, the mixer 116 outputs two heterodyne frequencies, the first of which is equal to the difference between the excitation frequency $f_{Excit}$ and the switching frequency $f_{Switch}$ of the mixing signal $V_{Mix}$. It is this first heterodyne that is referred to herein as the intermediate frequency $f_{Int}$. The second heterodyne output from the mixer 116 is equal to the sum of the excitation frequency $f_{Excit}$ and the switching frequency $f_{Switch}$. For example, if the excitation frequency $f_{Excit}$ is 20 MHz as in FIGS. 4A and 5A, and the switching frequency $f_{Switch}$ is 16 MHz as in FIGS. 4B and 5B, then the intermediate frequency $f_{Int}$ (the first heterodyne) is equal to 4 MHz, while the second heterodyne is equal to 36 MHz (assuming the mixer 116 is an ideal mixer).

FIG. 4C shows a time domain representation of an example frequency-downshifted signal $V_{Int}$ having an intermediate frequency $f_{Int}$ of 4 MHz. For ease of illustrating the down-shifting concept, the frequency-downshifted signal $V_{Int}$ is modeled assuming no time-varying amplitude modulation (for example, by the biological object 108). FIG. 5C shows a frequency domain representation of the example frequency-downshifted signal $V_{Int}$ of FIG. 4C. As shown in FIG. 5C, while some of the power of the frequency-downshifted signal $V_{Int}$ is concentrated at the intermediate frequency $f_{Int}$ of 4 MHz, power also is concentrated at the second heterodyne frequency of 36 MHz. Additionally, power also can be present in both super- and sub-harmonics due to folding with the harmonics of the switching frequency $f_{Switch}$. The second heterodyne and these other frequency components can be filtered out as described further below.

The frequency-downshifted signal $V_{Int}$ output from the mixer 116 is subsequently passed through a filter 120 to provide a filtered signal $V_{Filter}$. In some implementations, the filter 120 is a bandpass filter (and will hereinafter also be referred to as such), and in some specific implementations, a narrow bandpass filter. The bandpass filter 120 removes undesired low and high frequency components ensuring that unwanted aliases or harmonics (such as those shown in FIG. 5C) introduced by the mixer 116 are removed from the frequency-downshifted signal $V_{Int}$. As described above, the switching frequency $f_{Switch}$ is selected or adjusted by the controller 118 such that the intermediate frequency $f_{Int}$ of the down-shifted signal $V_{Int}$ is positioned at the center frequency of the filter 120. The bandwidth of the filter 120 should be higher than the bandwidth of the modulating signal but narrow enough to filter out the adjacent harmonics. FIG. 4D shows a time domain representation of an example filtered signal $V_{Filter}$ having an intermediate frequency $f_{Int}$ of 4 MHz. FIG. 5D shows a frequency domain representation of the example filtered signal $V_{Filter}$ of FIG. 4D. As shown in FIG. 5D, the other frequency components formerly present in the downshifted signal $V_{Int}$ have been removed by the filter 120. This is because the filter 120 effectively removes the components defined by the second term in equation (1).

In some implementations, the filter 120 is a passive filter having a fixed passband such as a quartz, piezoelectric, crystal, ceramic or surface acoustic wave (SAW) filter. Such filters generally have higher quality (Q) factors than traditional electronic filters and consume substantially zero power. In some other passive filter implementations, the filter 120 can be implemented as a circuit using resistors, capacitors, inductors, or transformers. In some other implementations, the filter 120 can be an active filter, but active filters by definition require a power source, and as such, may be undesirable for long-term wearable applications.

As an example of one specific cardiovascular use case in which the mixer 116 is a switching circuit and in which the filter 120 is a narrow bandpass filter, the filter can be selected or designed to have a 15 kHz passband centered at a center frequency of 500 kHz. In such an example use case, the excitation frequency $f_{Excit}$ can be 20 MHz and the switching frequency $f_{Switch}$ can be 19.5 MHz. As described above, the controller 118 functions to set the switching frequency $f_{Switch}$ such that the intermediate frequency $f_{Int}$—equal to the difference between the excitation frequency $f_{Excit}$ and the switching frequency $f_{Switch}$—is substantially equal to the center frequency of the bandpass filter 120. Thus, the intermediate frequency $f_{Int}$ and the center frequency of the bandpass filter 120 would both be substantially equal to 500 kHz, and the filter 120 would pass frequency components between 492.5 kHz and 507.5 kHz. In such a use case, the down-shifted signal $V_{Int}$ would be amplitude-modulated synchronous with the user's heartbeat. A human heart rate is generally on the order of 1 Hz (60 beats per minute), and almost never more than 4 Hz (even when a user is running at full capacity). As such, even conservatively allowing for a heart rate of 1000 Hz (1 kHz), the sidebands of the down-shifted signal $V_{Int}$ in the frequency domain would be centered at 499 kHz and 501 kHz—well within the passband of 492.5-507.5 kHz.

Leaving this example use case and referring generally back to the signal processing circuit 104, in some implementations, the filtered signal $V_{Filter}$ is then passed through a buffer 122. For example, passing the filtered signal $V_{Filter}$ through the buffer 122 can be advantageous for increasing the amplitude of the filtered signal $V_{Filter}$ to match the dynamic range of the subsequent analog-to-digital converter (ADC) 124. In some implementations, the buffer 122 is implemented as an amplifier. In an example of one particular use case, the buffer 122 can include a summing amplifier that adds an inverted sinusoid signal with center frequency $f_{Int}$ to the filtered signal $V_{Filter}$ to subtract the high intermediate amplitude. As a result, the amplitude modulation may be amplified to provide a favorable dynamic range for the ADC 124. The buffered signal $V_{Buf}$ output from the buffer 122 is then sampled by the ADC 124. In some other implementations, a buffer 122 is not present and the ADC 124 directly samples the filtered signal $V_{Filter}$.

The ADC 124 samples the filtered and buffered signal $V_{Buf}$ at a sampling frequency $f_{Sample}$ to produce a digital signal $V_{Dig}$. In various implementations, the ADC 124 undersamples the signal $V_{Buf}$. In other words, the undersampling frequency $f_{Sample}$ does not satisfy the Nyquist sampling criteria, which would require that the sampling frequency $f_{Sample}$ be greater than twice the intermediate frequency $f_{Int}$. However, the undersampling frequency $f_{Sample}$ used by the ADC 124 to sample the signal $V_{Buf}$ does satisfy the Shannon sampling criteria. That is, the undersampling frequency $f_{Sample}$ is greater than twice the bandwidth of the signal $V_{Buf}$. In some implementations, a proper or sufficient undersampling frequency $f_{Sample}$ can be determined from equation (2) below:

$$f_{sample} = \frac{1}{x * T_P + T_P/4}, \qquad (2)$$

where $T_P$ is a time period corresponding to the inverse of the intermediate frequency $f_{Int}$, and x is the undersampling ratio. The undersampling ratio (in this particular case) is the ratio of the intermediate frequency to the undersampling frequency. The undersampling ratio x determines how many wavelengths or periods of the signal will be skipped before a next value is sampled.

In some implementations, the frequency-downshifted signal $V_{Int}$ is sampled at at least two phases by the ADC 124. That is, the frequency-downshifted signal $V_{Int}$ is sampled at a first phase and also at a second phase, which in some implementations is 90 degrees (or π/2 radians) offset from the first phase. The fraction $T_P/4$ in equation (2) ensures that the second phase is offset 90 degrees from the first phase. However, for a sinusoidal signal, four sampling points for each period of the signal are generally needed or desired to reconstruct the signal with absolute amplitude and phase.

Advantageously, the I and Q channels traditionally needed to demodulate a signal are not needed in this scheme. More specifically, the I and Q channels are not needed because the in-phase and quadrature-phase components are still present in the filtered, frequency-downshifted signal $V_{Filter}$ when it is undersampled by the ADC 124 at the two (or four) distinct phases. Furthermore, because of the frequency-downshifting by the mixer 116 and the undersampling by the ADC 124, a low speed (and thus low power) ADC can be used. In some implementations, the ADC 124 has a resolution of at least 18 bits, and in some implementations, a resolution of at least 24 bits.

Because the Shannon sampling theorem is satisfied, the resultant demodulated digital signal $V_{Dig}$ permits reconstruction of the modulating signal of interest (for example, the arterial distension signal shown in FIG. 3). Thus, the combination of downshifting the carrier frequency of the detected signal $V_{Mod}$ to an intermediate frequency $f_{Int}$, filtering the frequency-downshifted signal to provide a filtered signal $V_{Filter}$, and subsequently undersampling the filtered signal results in a demodulated digital signal $V_{Dig}$ that can be used to reconstruct both the absolute amplitude and the phase of the modulating signal of interest. In some implementations, the digital signal $V_{Dig}$ is then stored in a memory and/or communicated through an interface to another component of the bioimpedance sensor 100.

In some implementations, the bioimpedance sensor 100 also includes a digital-to-analog converter (DAC) for reconstructing the modulating signal from the demodulated digital signal $V_{Dig}$. The DC value, the real component of the voltage amplitude ($V_{Re}$), the imaginary component of the voltage amplitude ($V_{Im}$), the impedance (Z), and the phase (θ) of the reconstructed signal can be determined by equations (3)-(7), respectively, shown below:

$$DC = \frac{V_1 + V_3}{2} = \frac{V_2 + V_4}{2}, \quad (3)$$

$$V_{Re} = \frac{V_1 - V_3}{2}, \quad (4)$$

$$V_{Im} = \frac{V_2 - V_4}{2}, \quad (5)$$

$$Z = \sqrt{(V_{Re}^2) + (V_{Im}^2)}, \quad (6)$$

$$\theta = \arctan\frac{V_{Im}}{V_{Re}}, \quad (7)$$

where $V_1$, $V_2$, $V_3$ and $V_4$ are the values of the samples taken by the ADC 124 at four distinct 90 degree offset phases within each period.

Figure 6:
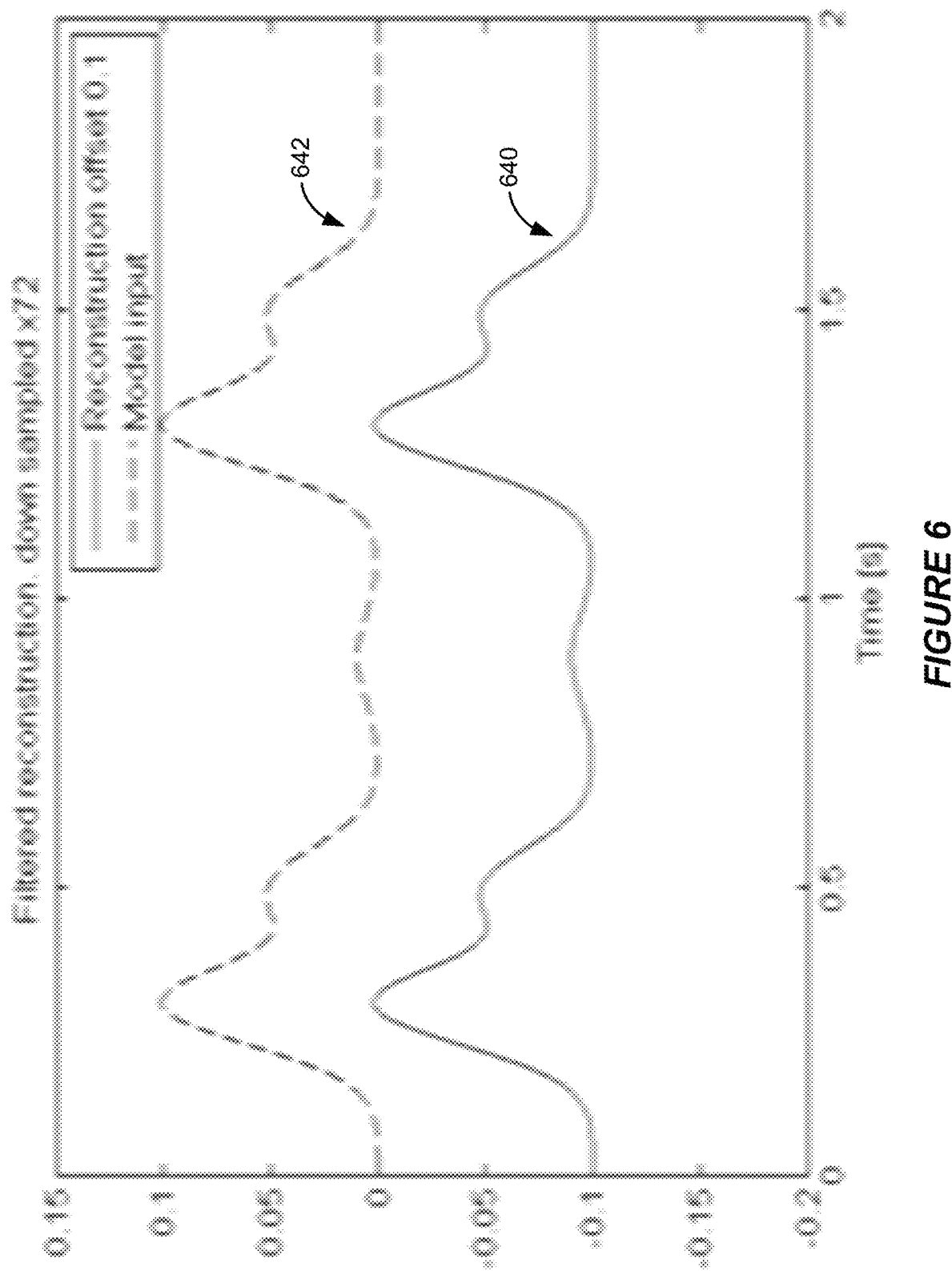
FIG. 6 shows a time domain representation of a reconstructed arterial distension signal 640 obtained using a simulation of the bioimpedance sensor of FIG. 1.

FIG. 6 shows a time domain representation of a reconstructed arterial distension signal 640 obtained using a simulation of the bioimpedance sensor 100 of FIG. 1. More specifically, FIG. 6 shows the reconstructed arterial distension signal 640 after reconstructing the digital signal $V_{Dig}$ output from the ADC 124 of FIG. 1. In this example, the dashed line represents a model arterial distension signal 642 (the modulating signal) used in the simulation, and the solid line represents the reconstructed arterial distension signal 640 obtained after the reconstruction (the offset is introduced to show the comparison). In the simulation, the excitation frequency $f_{Ext}$ was 2 MHz, the switching frequency $f_{Switch}$ was 1.5 MHz, and the undersampling ratio x was 72. In the example shown in FIG. 6, the ideal case of zero noise was assumed, and the reconstructed arterial distension signal 640 is a perfect reconstruction of the model arterial distension signal 642. In actuality, noise can result in some deviation of the reconstructed signal relative to the actual modulating signal. In some implementations, the controller 118 also can be operable to perform additional processing on the reconstructed signal, for example, to correct for the presence of deviation due to noise or other non-idealities. For example, a wavelet filtering operation can be used in some implementations to correct for noise.

In some implementations, the controller 118 also can control the ADC 124 to adjust the undersampling frequency $f_{Sample}$ used by the ADC 124 to reduce the undersampling frequency as much as possible while ensuring that the Shannon sampling criterion is satisfied, for example, based on knowledge of the modulating signal of interest. For example, the bioimpedance sensor 100 can include a memory that stores a lookup table that matches undersampling frequencies for particular modulating signals of interest. In some implementations, the bioimpedance sensor 100 can be operable to enable a user to select a modulating signal to be monitored (such as an arterial distention signal), and based on the user's selection, the controller 118 can adjust the undersampling frequency $f_{Sample}$ based on a result obtained from the lookup table.

Figure 7:
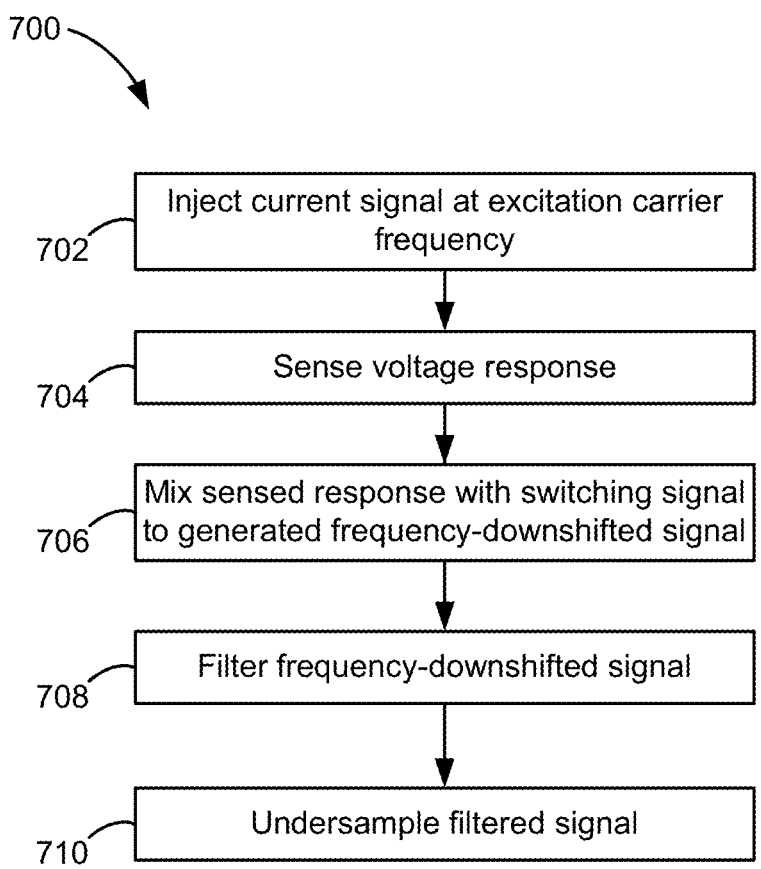
FIG. 7 shows a flowchart of an example process flow for demodulating an amplitude-modulated signal according to some implementations.

FIG. 7 shows a flowchart of an example process flow 700 for demodulating an amplitude-modulated signal according to some implementation. In some implementations, the process flow 700 begins in block 702 with injecting an excitation current signal $I_{Excit}$ at an excitation frequency $f_{Excit}$ into a region of interest of a biological object. In block 704, an amplitude-modulated (and generally phase-modulated) voltage response to the excitation signal $I_{Excit}$ is detected and sensed by a sensing circuit (for example, the amplifier 114) to generate a sensed signal $V_{Sense}$. In block 706, the sensed signal $V_{Sense}$ is mixed (for example, by the mixer 116) with a mixing signal $V_{Mix}$ having a switching frequency $f_{Switch}$ to generate a frequency-downshifted signal $V_{Int}$ having an intermediate carrier frequency $f_{Int}$. In block 708, the frequency-downshifted signal $V_{Int}$ is filtered (for example, by the filter 120) to provide a filtered signal $V_{Filter}$. In block 710, the filtered signal $V_{Filter}$ is undersampled by a sampler (for example, the ADC 124) to provide a demodulated digital signal $V_{Dig}$ usable to recover or reconstruct a modulating signal of interest.

As initially described above, in some implementations it can be desirable to inject multiple excitation frequencies into a medium, such as a biological object 108 substantially simultaneously. For example, assume that it is desired to excite a region of interest of a biological object 108 with a first 20 MHz excitation signal and a second 200 kHz excitation signal substantially or approximately simultaneously. One way to achieve this is for the excitation circuit 102 to sequentially and alternately apply the first excitation signal for a brief duration of time and then to apply the second excitation signal for a brief duration of time before again applying the first excitation signal and repeating. In such a didactic example, during the time when the first excitation signal is applied, the signal processing circuit 104, and more specifically the mixer 116, mixes the first resultant voltage response signal with a first mixing signal at a first mixing frequency to obtain a first frequency-shifted signal at an intermediate frequency. Similarly, during the time when the second excitation signal is applied, the signal processing circuit 104, and more specifically the mixer 116, mixes the second resultant voltage response signal with a second mixing signal at a second mixing frequency to obtain a second frequency-shifted signal also at the same intermediate frequency. In this way, both the first and the second frequency-shifted signals can be filtered using the same filter. In this way, the signal processing circuit 104 does not require any additional components, at least not until after the ADC 124. The signal processing circuit 104 would then synchronize the captured sample(s) from the ADC according to eq. (2) so that the samples taken from the first filtered frequency-shifted signal are routed to a separate buffer from that of the samples taken from the second filtered frequency-shifted signal. As long as the first and the second excitation frequencies are changed fast enough, the ADC 124 would still capture any dynamic voltage and frequency response from the excited tissues. It should also be appreciated that more than two excitation frequencies may be used.

Another method for simultaneous excitation with multiple frequencies is to inject all of the different desired excitation signals concomitantly. One way to accomplish this is to cause the mixer 116 to change mixing frequencies sequentially and alternately so that each voltage response signal can be frequency-shifted and filtered by the filter 120 before undersampling by the ADC 124.

Additionally, it should also be appreciated that, in some other implementations, the excitation signal generator 106 can be a voltage source that provides the excitation signal in the form of an electrical voltage signal, and more specifically, an RF AC voltage signal. In such case, the sensed amplitude-modulated signal would be an electrical current signal. However, the basic operation of the signal processing circuit 104 would be generally unchanged.

It should also be appreciated that practical RF AC excitation signal generators have neither zero impedance nor infinite impedance, and thus, whether a current source or a voltage source is used, both will produce time-varying current signals as well as time-varying voltage signals, however trivial. For example, an RF AC current source will produce a time-varying current signal as well as a generally trivial time-varying voltage signal. Similarly, an RF AC voltage source will produce a time-varying voltage signal as well as a generally trivial time-varying current signal. However, in some other implementations, the excitation signal generator can be operable to provide an excitation signal that includes both a non-trivial time-varying voltage component as well as a non-trivial time-varying current component.

It should also be appreciated that the signal processing circuit 104 is not limited to bioimpedance sensor applications. To the contrary, the signal processing circuit 104 can be used in any of a variety of sensing applications including impedance sensing applications not involving a biological object.

Figure 8:
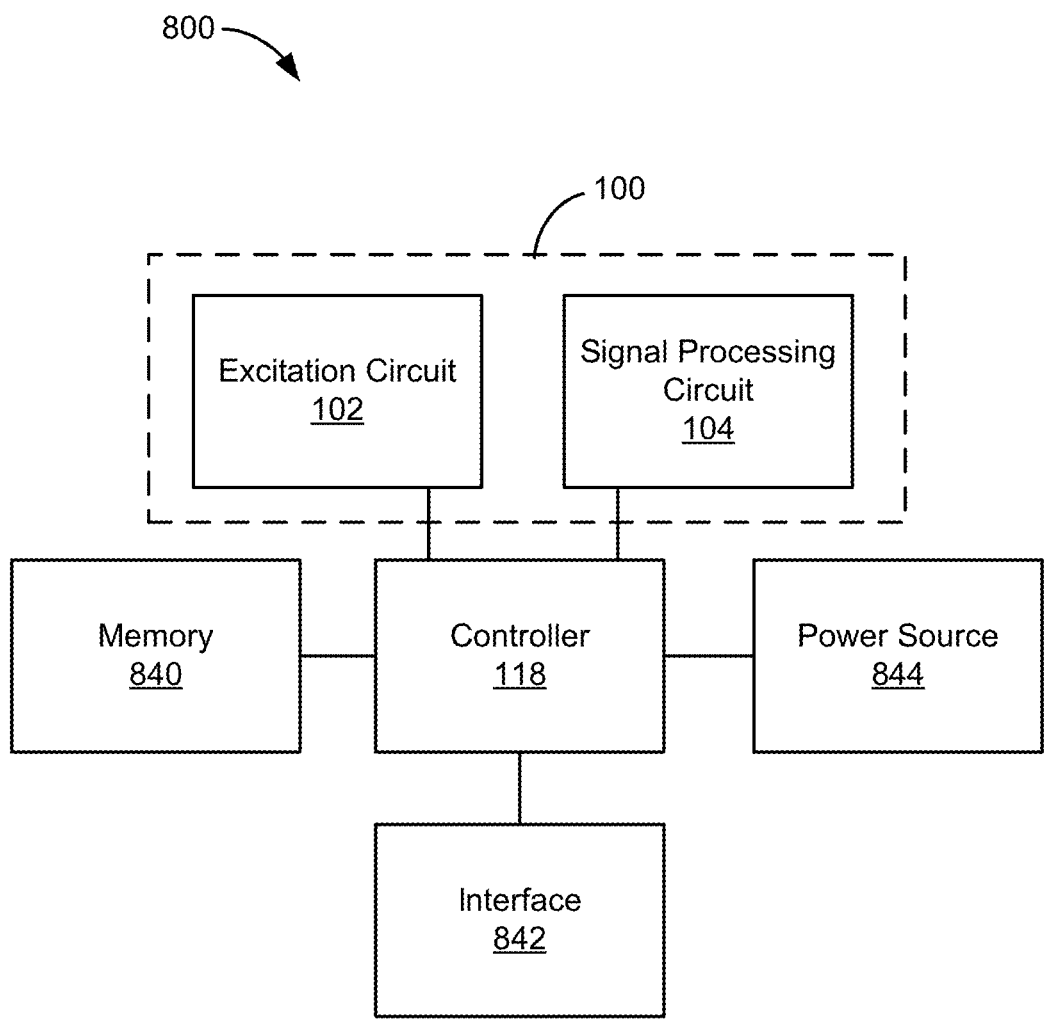
FIG. 8 shows a system diagram of a device that includes the bioimpedance sensor of FIG. 1.

FIG. 8 shows a system diagram of a device 800 that includes the bioimpedance sensor 100 of FIG. 1. As shown, the controller 118 controls the operations of the excitation circuit 102 as well as the signal processing circuit 104. The controller also receives the digital voltage signal $V_{Dig}$ from the ADC 124. While the controller 118 is shown and described as a single component, in some implementations, the controller 118 can refer to two or more different controllers or processing components. In some implementations, one or more of such controllers or processing components can be implemented with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

As described above, the controller 118 may store the digital voltage signal $V_{Dig}$ in a memory 840. The memory 840 also can include code or other executable instructions for execution by the controller 118. The memory 840 can include one or more memory components. In some implementations, one or more of the memory components can be implemented as a NOR- or NAND-based Flash memory array. In some other implementations, one or more of the memory components can be implemented as a different type of non-volatile memory. Additionally, in some implementations, one or more of the memory components can include a volatile memory array such as, for example, a type of RAM.

In some implementations, the controller 118 can communicate data stored in the memory 840 or data received directly from the signal processing circuit 104 to an interface 842. In some implementations, the interface 842 can be a memory interface for receiving and storing data in an external memory such as a removable memory device. In some other implementations, the interface 842 can be a communication interface enabling the transfer of the data to an external computer when connected. Similarly, the interface 842 also can enable the device 800 to receive data from such a connected external computer.

A power supply 844 can provide power to some or all of the components in the device 800. The power supply 844 can include one or more of a variety of energy storage devices. For example, the power supply 844 can be a rechargeable battery, such as a nickel-cadmium battery or a lithium-ion battery. In implementations using a rechargeable battery, the rechargeable battery may be chargeable using power coming from, for example, a wall socket or a photovoltaic device or array. Alternatively, the rechargeable battery can be wirelessly chargeable. The power supply 844 also can include a renewable energy source, a capacitor, or a solar cell, including a plastic solar cell or solar-cell paint.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, the separation of various system components in the implementations described above should not be understood as requiring such separation in all implementations. Additionally, other implementations are within the scope of the following claims. In some cases, the actions recited in the claims can be performed in a different order and still achieve desirable results.

What is claimed is:
1. A device, comprising:
   a sensing circuit operable to sense an amplitude-modulated signal having a carrier frequency;
   a mixer operable to mix the amplitude-modulated signal with a mixing signal having a mixing frequency to provide a frequency-downshifted signal having an intermediate frequency less than the carrier frequency and greater than a modulating frequency of a modulating signal creating amplitude modulation of the amplitude-modulated signal;
   a filter operable to filter the frequency-downshifted signal to provide a filtered signal, the filter including a bandpass filter having a passband, the passband having a fixed center frequency;

a sampler operable to undersample the filtered signal at an undersampling frequency to provide a digital signal, the digital signal being representative of the modulating signal;

a memory comprising a lookup table matching a plurality of undersampling frequencies to a plurality of modulating signal types;

a controller operable to set the mixing frequency of the mixing signal to provide the frequency-downshifted signal with the intermediate frequency equal to the fixed center frequency of the passband, and the intermediate frequency being equal to a difference between the carrier frequency and the mixing frequency, wherein the controller is further operable to reconstruct an absolute amplitude and a phase of the digital signal, wherein the controller is further operable to adjust the undersampling frequency according to the lookup table and a modulating signal type of the modulating signal;

a first electrode adapted to couple with a biological object;

an excitation signal generator operable to generate at least one excitation signal at the carrier frequency, the first electrode being adapted to provide the at least one excitation signal to the biological object, the amplitude-modulated signal being representative of a response of the biological object to the at least one excitation signal; and a second electrode operable to receive the amplitude-modulated signal and to pass the amplitude-modulated signal to the sensing circuit, the second electrode being adapted to couple with the biological object;

a power source;

a wearable housing that at least partially encompasses the sensing circuit, the mixer, the filter, the sampler, and the power source; and a strap or band adapted to couple the wearable housing to the biological object.

2. The device of claim 1, wherein the amplitude-modulated signal is phase-modulated relative to the modulating signal.

3. The device of claim 1, wherein the modulating signal is representative of an impedance of the biological object.

4. The device of claim 3, wherein the carrier frequency is greater than or equal to 1 MHz.

5. The device of claim 3, wherein:
the at least one excitation signal includes an electrical current signal; and
the response of the biological object to the at least one excitation signal includes a voltage response of the biological object to the at least one excitation signal based on the impedance.

6. The device of claim 3, wherein:
the excitation signal includes an electrical voltage signal; and
the amplitude-modulated signal includes an electrical current signal representative of a current response of the biological object to the excitation signal based on the impedance.

7. The device of claim 1, wherein the undersampling frequency is greater than twice a bandwidth of the filtered signal.

8. The device of claim 1, wherein the filter includes a passive filter.

9. The device of claim 1, wherein the controller is operable to set the carrier frequency.

10. The device of claim 1, wherein the mixer includes a switching device, and wherein the switching device includes a single pole, single throw (SPST) switch or a single pole, double throw (SPDT) switch.

11. The device of claim 1, wherein the mixing signal is a square wave signal.

12. The device of claim 1, wherein the excitation signal generator is operable to generate multiple excitation signals at different excitation frequencies simultaneously or alternately.

13. The device of claim 12, wherein each of the multiple excitation signals correspond to one of multiple amplitude modulated signals, wherein the mixer is operable to mix each of the multiple amplitude-modulated signals with one of multiple mixing signals, wherein each mixing signal corresponds to one of multiple mixing frequencies, and wherein the controller is configured to cause the mixer to change mixing frequencies sequentially and alternately so that each amplitude-modulated signal is filtered by the filter and then undersampled by the sampler.

14. A device, comprising:
means for sensing an amplitude-modulated signal having a carrier frequency;

means for mixing the amplitude-modulated signal with a mixing signal having a mixing frequency to provide a frequency-downshifted signal having an intermediate frequency less than the carrier frequency and greater than a modulating frequency of a modulating signal creating amplitude modulation of the amplitude-modulated signal;

filtering means for filtering the frequency-downshifted signal to provide a filtered signal, the filtering means including a bandpass filter having a passband, the passband having a fixed center frequency;

a means for storing a lookup table matching a plurality of undersampling frequencies to a plurality of modulating signal types;

sampling means for undersampling the filtered signal at an undersampling frequency to provide a digital signal, the digital signal being representative of the modulating signal;

means for setting the mixing frequency of the mixing signal to provide the frequency downshifted signal with the intermediate frequency equal to the fixed center frequency of the passband, and the intermediate frequency being equal to a difference between the carrier frequency and the mixing frequency, wherein the means for setting the mixing frequency is also operable to reconstruct an absolute amplitude and a phase of the digital signal, wherein the means for setting the mixing frequency is also operable to adjust the undersampling frequency according to the lookup table and a modulating signal type of the modulating signal;

first electrode means adapted to couple with a biological object;

excitation signal generator means operable to generate at least one excitation signal at the carrier frequency, the first electrode means being adapted to provide the at least one excitation signal to the biological object, the amplitude-modulated signal being representative of a response of the biological object to the at least one excitation signal;

second electrode means operable to receive the amplitude-modulated signal and to pass the amplitude-modulated signal to the means for sensing, the second electrode means being adapted to couple with the biological object;

a power source;

a wearable housing that at least partially encompasses the means for sensing, the means for mixing, the filtering means, the sampling means, the excitation signal generator means, the first electrode means, the second electrode means, and the power source; and an adhesive adapted to couple the wearable housing to the biological object.

15. The device of claim 14, wherein the modulating signal is representative of an impedance of the biological object.

16. The device of claim 15, wherein the carrier frequency is greater than or equal to 1 MHz.

17. The device of claim 15, wherein:

the at least one excitation signal includes an electrical current signal; and the response of the biological object to the at least one excitation signal includes a voltage response of the biological object to the at least one excitation signal based on the impedance.

18. The device of claim 14, wherein the excitation signal generator means is operable to generate multiple excitation signals at different excitation frequencies simultaneously or alternately.

19. The device of claim 18, wherein each of the multiple excitation signals correspond to one of multiple amplitude modulated signals, wherein the means for mixing is operable to mix each of the multiple amplitude-modulated signals with one of multiple mixing signals, wherein each mixing signal corresponds to one of multiple mixing frequencies, and wherein the means for setting the mixing frequency also comprises a means for causing the means for mixing to change mixing frequencies sequentially and alternately so that each amplitude-modulated signal is filtered by the filtering means and then undersampled by the sampling means.

* * * * *